US010743830B2

(12) United States Patent
Qi et al.

(10) Patent No.: US 10,743,830 B2
(45) Date of Patent: Aug. 18, 2020

(54) METHOD AND APPARATUS FOR SCATTER CORRECTION IN POSITION EMISSION TOMOGRAPHY (PET) IMAGING BY PERFORMING A SHORT PET SCAN IN AN EXTENDED REGION TO ESTIMATE SCATTER COMING FROM OUTSIDE OF THE FIELD OF VIEW (FOV)

(71) Applicant: CANON MEDICAL SYSTEMS CORPORATION, Otawara-shi (JP)

(72) Inventors: Wenyuan Qi, Lake Bluff, IL (US); Chung Chan, Glenview, IL (US); Li Yang, Schaumburg, IL (US); Evren Asma, Buffalo Grove, IL (US)

(73) Assignee: CANON MEDICAL SYSTEMS CORPORATION, Otawara-shi (JP)

(*) Notice: Subject to any disclaimer, the term of this patent is extended or adjusted under 35 U.S.C. 154(b) by 73 days.

(21) Appl. No.: 16/209,551

(22) Filed: Dec. 4, 2018

(65) Prior Publication Data
US 2020/0170605 A1  Jun. 4, 2020

(51) Int. Cl.
*A61B 6/02* (2006.01)
*A61B 6/00* (2006.01)
(Continued)

(52) U.S. Cl.
CPC ............ *A61B 6/5235* (2013.01); *A61B 6/037* (2013.01); *A61B 6/5205* (2013.01);
(Continued)

(58) Field of Classification Search
CPC ..... A61B 6/5235; A61B 6/037; A61B 6/5205; A61B 6/5282; A61B 6/488; G01T 1/2985
See application file for complete search history.

(56) References Cited

U.S. PATENT DOCUMENTS 9,872,664 B1  1/2018 Jin et al.
2004/0030246 A1  2/2004 Townsend et al.
(Continued)

FOREIGN PATENT DOCUMENTS

WO  WO 2016/092428 A1  6/2016

OTHER PUBLICATIONS

Iatrou Maria, et al. "Out-of-Field Scatter Estimation in 3D Whole body PET", 2009 IEEE Nuclear Science Symposium Conference Record, M13-330, pp. 3886-3888.
(Continued)

*Primary Examiner* — David P Porta
*Assistant Examiner* — Mamadou Faye
(74) *Attorney, Agent, or Firm* — Oblon, McClelland, Maier & Neustadt, L.L.P.

(57) ABSTRACT

A method and apparatus is provided to correct for scatter in a positron emission tomography (PET) scanner, the scatter coming from both within and without a field of view (FOV) for true coincidences. For a region of interest (ROI), the outside-the-FOV scatter correction are based on attenuation maps and activity distributions estimated from short PET scans of extended regions adjacent to the ROI. Further, in a PET/CT scanner, these short PET scans can be accompanied by low-dose X-ray computed tomography (CT) scans in the extended regions. The use of short PET scans, rather than full PET scans, provides sufficient accuracy for outside-the-FOV scatter corrections with the advantages of a lower radiation dose (e.g., low-dose CT) and requiring less time. In the absence of low-dose CT scans, an atlas of attenuation maps or a joint-estimation method can be used to estimate the attenuation maps for the extended regions.

20 Claims, 13 Drawing Sheets

(51) Int. Cl.
G01T 1/29 (2006.01)
A61B 6/03 (2006.01)

(52) U.S. Cl.
CPC .......... *A61B 6/5282* (2013.01); *G01T 1/2985* (2013.01); *A61B 6/488* (2013.01)

(56) References Cited

U.S. PATENT DOCUMENTS

| | | |
|---|---|---|
| 2007/0106154 A1 | 5/2007 | Conti |
| 2009/0175562 A1* | 7/2009 | Pan .................. A61B 6/032 382/312 |
| 2018/0120459 A1 | 5/2018 | Andreyev et al. |

OTHER PUBLICATIONS

C.H. Holdsworth, et al. "Performance Analysis of an Improved 3-D PET Monte Carlo Simulation and Scatter Correction", IEEE Transactions on Nuclear Science, vol. 49, No. 1, Feb. 2002, pp. 83-89.

Watson, C.C., et al. "A single Scatter Simulation Technique for Scatter Correction in 3D PET," Three-Dimensional Image Reconstruction in Radiology and Nuclear Medicine, 255-268, (1996).

Watson, C.C., "Extension of Single Scatter Simulation to Scatter Correction of Time-of-Flight PET," IEEE Med. Imag. Conf. Rec, (2005).

Zaidi H., "Scatter Modelling and Correction Strategies in Fully 3-D PET," Nuclear Medicine Communications 22, 1181-1184, (2001).

Qi, J., et al., "Scatter Correction for Positron Emission Mammography," Physics in Medicine and Biology 47(15), 2759-2774, (2004).

Accorsi, R. et al."Optimization of a Fully 3D Single Scatter Simulation Algorithm for 3D PET," Physics in Medicine and Biology 49(12), 2577-2598, (2004).

Ye, J., et al. "Scatter Correction with Combined Single-Scatter Simulation and Monte Carlo Simulation for 3D PET," IEEE Med. Imag. Conf. Rec, (2014).

C. M. Laymon, et al. "Characterization of Single and Multiple Scatter From Matter and Activity Distribution Outside-the-FOV in 3D PET", TNS 51, 10-15, (2004).

Andriy Andreyev, et al. "Solving Outside-Axial-Field-of-View Scatter Correction Problem in PET Via Digital Experimentation," Proc. SPIE 9783, 97831N, Mar. 25, 2016.

* cited by examiner

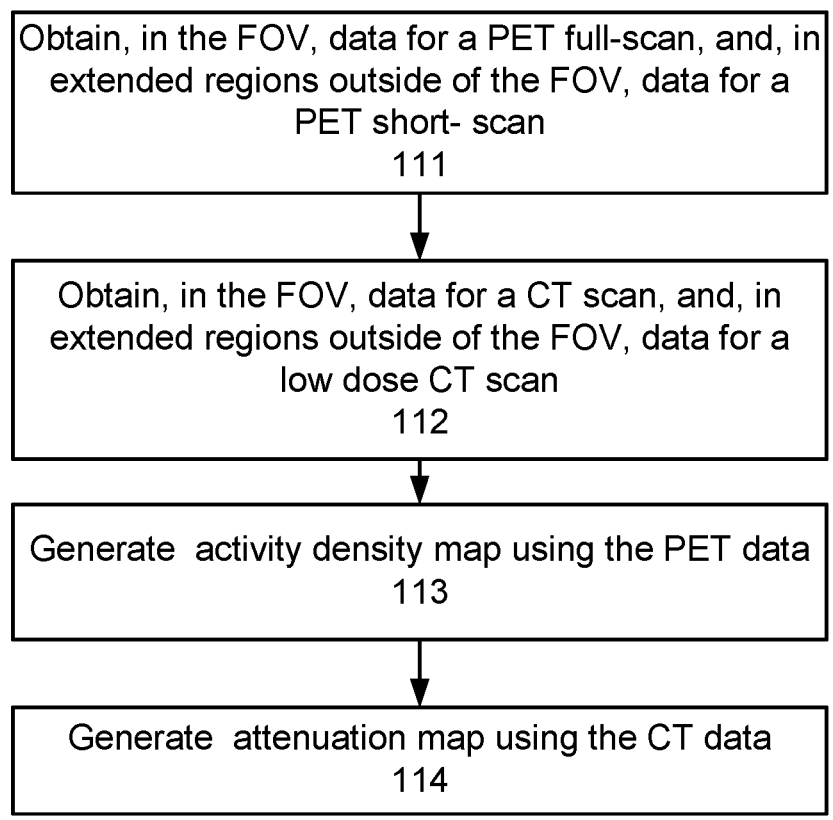

Obtain, in the FOV, data for a PET full-scan, and obtain, in extended regions outside of the FOV, data for a PET short- scan
111

Apply joint-estimation method to the PET data to generate both the attenuation map and the activity density map for both in and outside of the FOV
115

METHOD AND APPARATUS FOR SCATTER CORRECTION IN POSITION EMISSION TOMOGRAPHY (PET) IMAGING BY PERFORMING A SHORT PET SCAN IN AN EXTENDED REGION TO ESTIMATE SCATTER COMING FROM OUTSIDE OF THE FIELD OF VIEW (FOV)

FIELD

This disclosure relates to improving positron emission tomography (PET) imaging based on single-bed (or few-bed) scans, as opposed to a multi-bed whole-body scan. The single bed scan is augmented with short PET scans performed in the extended regions to either side of the field of view (FOV) of the single bed scan, and these short-extended scans are used to estimate attenuation maps and activity distributions in the extended regions forming the basis for outside-the-FOV scatter correction of PET data inside the FOV.

BACKGROUND

Positron emission tomography (PET) is an imaging method in nuclear medicine based on the use of a weak radioactively marked pharmaceutical (a tracer) to image certain features of a body. PET images display the spatial distribution of the radiopharmaceutical enabling a doctor or clinician to draw conclusions about metabolic activities or blood flow, for example. Therefore, PET is a functional imaging technique that has applications in oncology, cardiology, and neurology, e.g., for monitoring tumors or visualizing coronary artery disease.

In PET imaging, a tracer agent is introduced into the patient to be imaged (e.g., via injection, inhalation, or ingestion). After administration, the physical and bio-molecular properties of the agent cause it to concentrate at specific locations in the patient's body. The actual spatial distribution of the agent, the intensity of the region of accumulation of the agent, and the kinetics of the process from administration to its eventual elimination are all factors that may have clinical significance.

During this process, a tracer attached to the agent will emit positrons, which is the anti-matter equivalent of the electron. When an emitted positron collides with an electron, the electron and positron are annihilated, resulting in the emission of a pair of gamma rays each having an energy of 511 keV and the two gamma rays traveling at substantially 180 degrees apart.

The spatio-temporal distribution of the tracer is reconstructed via tomographic reconstruction principles, e.g., by characterizing each detection event for its energy (i.e., amount of light generated), its location, and its timing. When two gamma rays are detected within a coincidence time window, they likely originate from the same positron annihilation event, and, therefore, are identified as being a coincidence pair. Drawing a line between their locations, i.e., the line-of-response (LOR), one can determine the likely location of the positron annihilation event. The timing information can also be used to determine a statistical distribution along the LOR for the annihilation based on a time-of-flight (TOF) information of the two gamma rays. By accumulating a large number of LORs, tomographic reconstruction can be performed to determine a volumetric image of the spatial distribution of radioactivity (e.g., tracer density) within the patient.

The detected coincidence events (called coincidences) can be classified into true coincidences and background events. The background events can be further subdivided into accidental coincidences and scattered coincidences. Accidental (or random) coincidences occur where the two gamma rays did not arise from the same annihilation event. Scattered coincidences occur when the two gamma rays did originate from the same annihilation, but where the true annihilation position does not lie on the LOR connecting the two photon positions. This can happen, e.g., when one gamma ray experiences Compton scatter within the patient, changing its direction of propagation.

Tomographic reconstruction has been widely applied to visualizing the anatomical information of patients. Tomographic reconstruction can be used in various modalities, including projection-based imaging, such as in X-ray computed tomography (CT), and emission-based imaging, such as in PET. Due to health concerns regarding exposure to radiation, doctors, scientist, and engineers in medical imaging strive to maintain radiation doses as low as reasonably achievable. This effort to maintain radiation doses as low as reasonably achievable motivates continued improvements in reconstructed image quality while decreasing the radiation doses and signal-to-noise ratios of the measured signals.

Accordingly, improved methods are desired for performing PET scatter correction and for improving the image quality of PET images by reducing noise and interfering signals. In PET imaging in particular, scatter correction (including outside-the-FOV scatter correction) plays a significant role in improving image quality while reducing the radiation exposure to patients.

BRIEF DESCRIPTION OF THE DRAWINGS

A more complete understanding of this disclosure is provided by reference to the following detailed description when considered in connection with the accompanying drawings, wherein:

FIG. 7A shows an example of a flow diagram for generating activity distributions and attenuation maps using, in the extended regions, short PET scans and low-dose computed tomography (CT) scans, according to one implementation;

FIG. 7C shows an example of a flow diagram for generating the activity distributions and the attenuation maps using the short PET scans and a joint-estimation method, according to one implementation;

DETAILED DESCRIPTION

Figure 1:
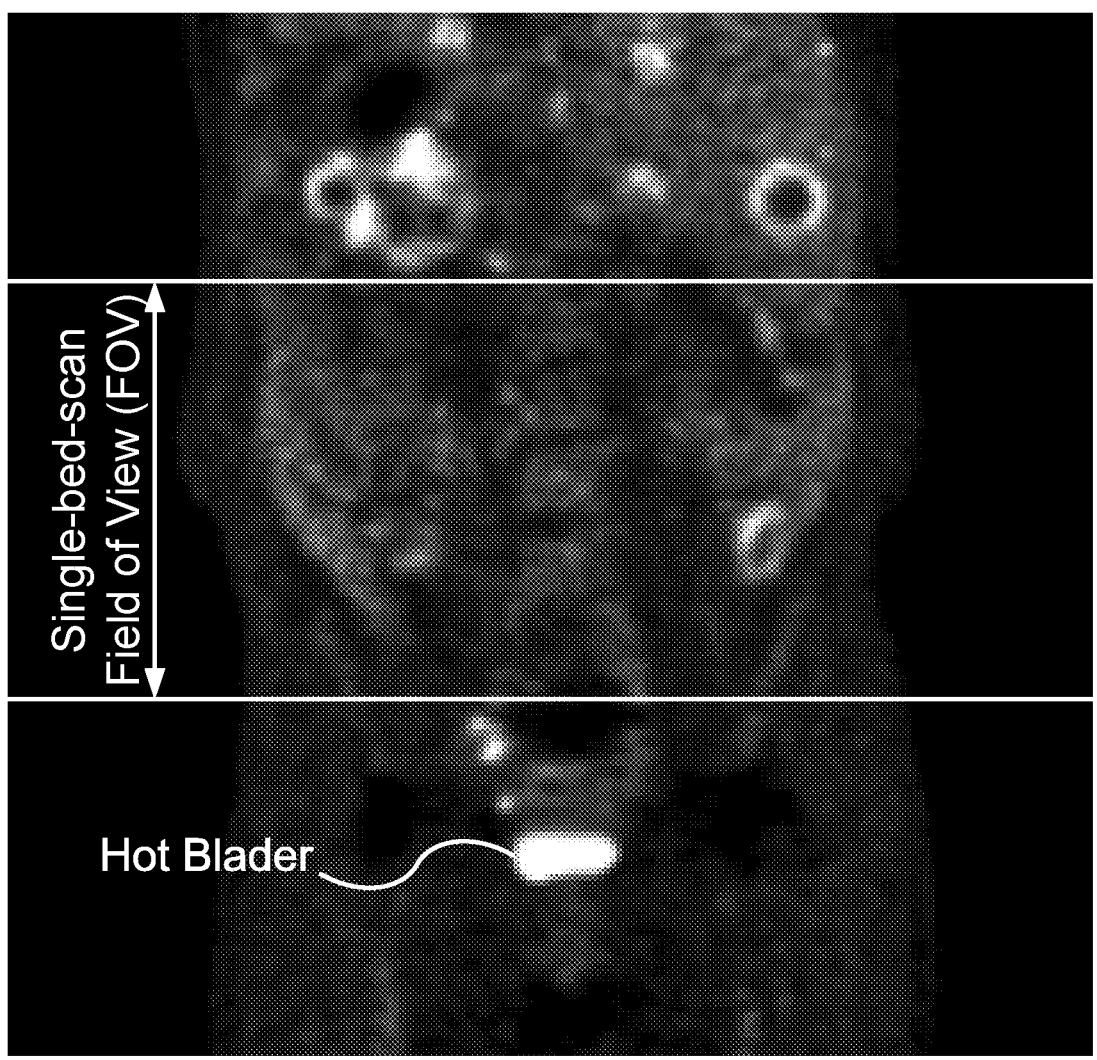
FIG. 1 shows an image of a positron emission tomography (PET) image from a multi-bed scan on top of which is superimposed a field of view (FOV) for a single-bed-position scan, according to one implementation.

Herein, the words "short" and "full" in conjunction with the word "scan" (e.g., "short scan" and "full scan") refer to the time duration of the PET scan—not the physical length or spatial extent of the scan, e.g., the number of bed positions over which the PET scan is acquired. Further, the phrases "multi-bed scan" and equivalently "multi-bed-position scan" refer to the spatial extent of a scan that is performed in multiple stages, each stage acquiring data from a field of view (FOV) of the PET (or CT) scanner that overlaps a portion of the subject/patient at the given bed position, wherein the scanner dwells for a predefine time interval, for example.

As discussed above, in positron emission tomography (PET), the measured coincidences include both true coincidences and a background signal (e.g., random coincidences). To improve the image quality of a reconstructed PET signal, it is desirable to estimate and account for this background signal. For example, the background signal can be accounted for by correcting the data using a baseline subtraction based on the estimated background signal, or, when a log-likelihood objective function is used to iteratively reconstruct a PET image, the log-likelihood expression can include a background-signal term based on the estimated background signal. The background signal includes counts due to random events and scatter events. In PET, the background signal is primarily made up of accidental coincidences (ACs), also known as randoms, and scatters.

For many annihilation events, only one photon of a pair of photons is detected because the other photon is absorbed or scattered out of plane of a PET detector ring. Further, some photon reaching the scintillating detectors of the PET detector ring are not detected due to a less than unity quantum efficiency of the detectors. Detection events in which only one of a pair of photons is detected can be referred to as "singles." If two singles from separate annihilations are detected within the coincidence timing window, then they are mistakenly registered as having arisen from the same annihilation. This is called an accidental coincidence (AC) event, also known as a random event. Stated differently, an AC event occurs when two unrelated singles are detected within a coincidence timing window.

Although most scattered photons in the body leave the detector plane undetected, some scattered photons are still detected and registered resulting in an incorrect LOR. In certain implementations, some of these scattered events resulting in incorrect LORs can be removed by energy discrimination because photons lose a fraction of their energy during the Compton interaction giving rise to the scatter event. Even so, some scattered photons (scatters) and some random coincidences (randoms) will inevitable be recorded, and, thus, the background signal includes the randoms and the scatters.

Various corrections can be performed on the PET data, resulting in better image quality. For example, gamma rays are attenuated as the propagate through the patient, detector elements vary in their detection efficiency, and random and scattered coincidences are recorded along with the true coincidence events. Correcting for these effects improves the image quality, resulting in clinically useful images and accurate quantitative information from PET studies.

First, consider the attenuation correction. Gamma rays that encounter more or denser material on their path from the annihilation site to the detectors are more likely to be absorbed or scattered (i.e., attenuated) than gamma rays that travel through sparser parts of the body. If images are reconstructed from sinograms without attenuation correction, then gamma rays from less dense areas (e.g., lungs) are over-represented (e.g., appear as though they are emitting more gamma rays than they actually are) and denser tissue are under-represented. In the absence of attenuation correction, the reconstructed imaged would be susceptible to artifacts that both impair the visual appearance of the image and also lead to inaccurate quantitation of tracer uptake. To apply attenuation correction, an attenuation map is generated whereby one can determine the attenuation through the patient for all LORs. For example, on a stand-alone PET scanner, this can be done with a transmission scan in which an external positron source is rotated around the patient and the attenuation of the transmitted gamma rays is determined. In a PET/CT scanners, the acquired CT image can be used used for PET attenuation correction. Further, in certain implementations, a joint-estimation method can be used to simultaneously derive both the attenuation map and the activity distribution for the PET data.

Second, the detector elements can be calibrated, and corrected for. Further, an axial/geometry based sensitivity correction can be applied to the data.

Third, the background signal can be estimated and accounted for in the reconstruction. For example, the PET image can be reconstructed using a penalized likelihood method to solve the optimization problem $$\hat{x} = \underset{x \geq 0}{\operatorname{argmin}}\{-L(x)\}$$

wherein x is the image to be reconstructed and L(x) is the Poisson likelihood function. The Poisson likelihood function can be expressed as $$L(x) = -\sum_j s_j x_j + \sum_i \log([Px]_i + r_i)$$

wherein $s_j$ is the sensitivity of voxel j, P is the system matrix whose elements represent the probability that the volume pixel of the reconstructed image corresponding to index j is within the line of response (LOR) associated with the $i^{th}$ detection event. Here $[\bullet]_i$ represents the $i^{th}$ element from a vector. The mean background signal is denoted by $r_i$, which includes counts due to random events and scatter events.

Referring now to the drawings, wherein like reference numerals designate identical or corresponding parts throughout the several views, FIG. 1 shows a PET image from a whole body scan. This image is knitted together from a series of single scans each corresponding to the single-scan width (i.e., the width of the single-bed-scan FOV) shown in FIG. 1. Thus, the whole-body scan can also be referred to as a multi-bed scan, in which the scan proceeds by the PET detector ring dwelling at each bed position in a series of bed positions. The PET detector ring dwells at each of the bed positions for a full-scan period before moving to the next bed location. As can be seen in FIG. 1, the image within the illustrated single-scan width is susceptible not only to scatter/background signal from gamma rays originating within the single-bed field of view (FOV), but is also susceptible to gamma rays originating outside of the FOV, especially the hot bladder, which has a high activity density. In a multi-bed (e.g., full-body) scan, the PET data is acquired for regions above (anterior) and below (posterior) the single-scan width illustrated in FIG. 1, enabling the estimation of an attenuation map and activity distribution for regions outside of the single-scan FOV.

In contrast, for a single-bed scan, PET scans are not generally acquired in the neighboring extended regions that neighbor the FOV of the single-bed scan, preventing the estimation of attenuation maps and activity distributions for extended regions outside of the single-scan FOV. Accordingly, in a single-bed scan, the methods proposed herein acquire additional data using a short extended PET scan in the neighboring extended regions to the posterior and anterior of the single-bed scan FOV. This additional data then enables the generation of attenuation maps and activity distributions for regions that are adjacent to but outside of FOV of the single-bed scan FOV. Using these outside-the-FOV attenuation maps and activity distributions, outside-the-FOV scatter correction can be performed for the single-scan PET data, thereby generating better image quality for the reconstructed PET image inside the FOV.

Figure 2A:
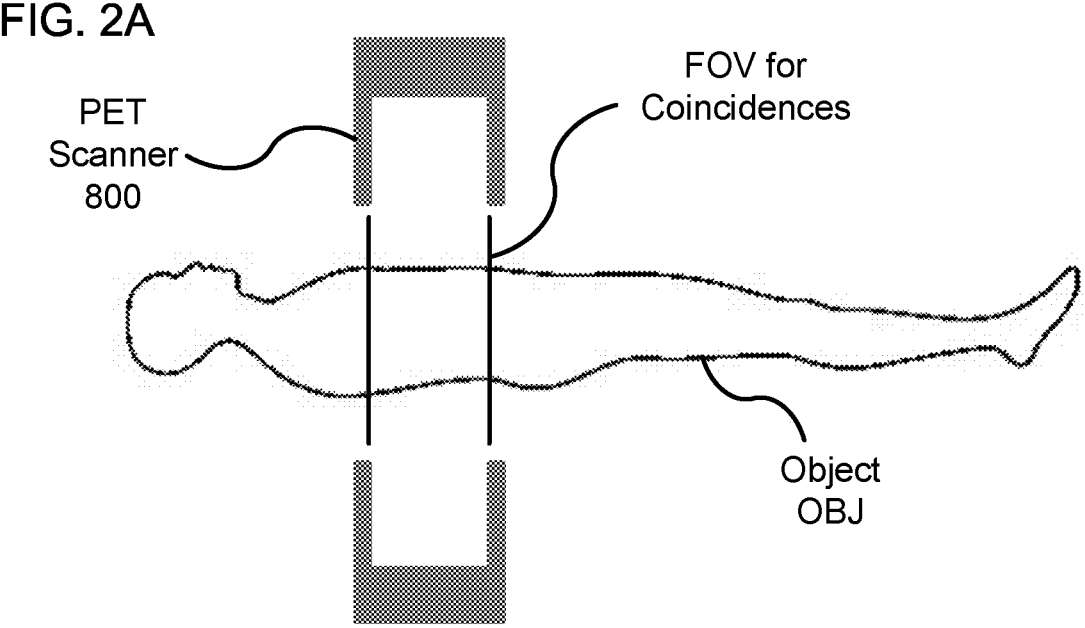
FIG. 2A shows a diagram for a FOV of true coincidences in a PET scanner, according to one implementation.

FIG. 2A shows a PET scanner 800 in relation to an object OBJ. FIG. 2A also shows the imaging FOV (i.e., the FOV for true coincidences) in which both gamma rays arrive at the detectors without undergoing scatter. For example, the FOV in FIG. 2A can be for true coincidences when a PET scanner 800 is performing a single-bed scan. Herein, the term "single-bed" refers to a PET scan in which the PET image is generated for only one bed position.

Figure 2B:
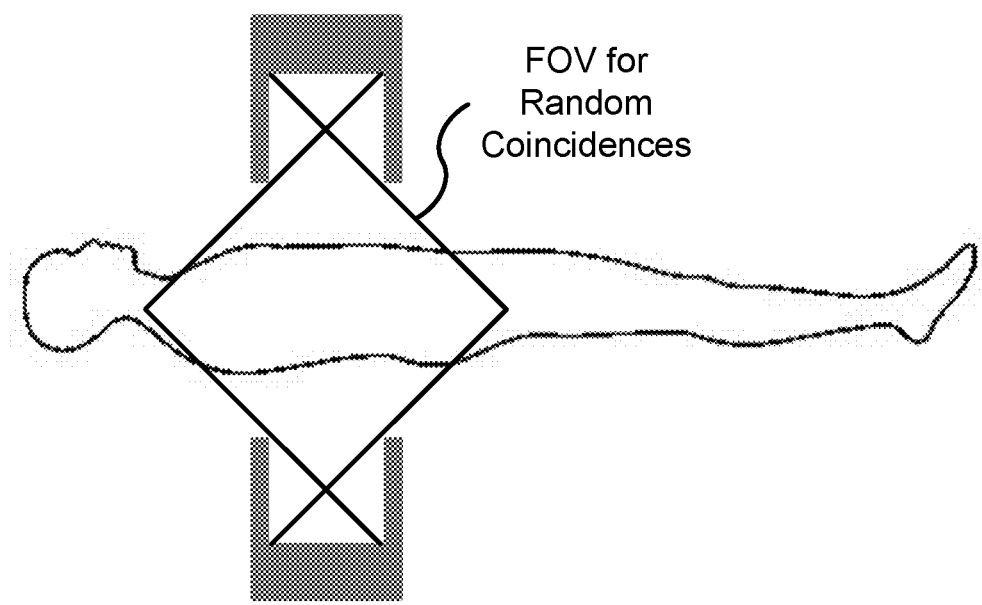
FIG. 2B shows a diagram for a FOV of random coincidences in the PET scanner, according to one implementation.

FIG. 2B shows a schematic diagram of the region in which gamma rays can originate giving rise to random coincidences. Thus, random coincidences can arise from regions outside of the imaging FOV (i.e., the FOV for true coincidences shown in FIG. 2A).

In two-dimensional (2D) and/or three-dimensional (3D) PET, the scatter effect is one of the most significant physical factors degrading the image quality. In a typical 3D PET system, scatter events can be between 30% and 50% of total detected events. scatter estimation can be used to correct for scatter in PET data. When the object is longer in and axially direction than the PET scanner, outside-the-FOV scatter (i.e. scattered gamma rays coming from outside the imaging FOV) should preferably be accounted for. Such outside-the-FOV scatter can exceed 40% of total scatter, especially when the PET system has a big bore opening without end shielding. Like the general scatter discussed above, outside-the-FOV scatter events can be viewed in two categories: (i) events that originate within the FOV where one or both of the detected photons scatter from matter located outside of the FOV and (ii) events that originate from annihilation events (i.e., activity) occurring outside of the FOV. For both categories, attenuation and activity distributions outside-the-FOV are required to model the detected scatter distribution.

For a gamma ray that scatters into the FOV from the outside of the FOV, two conditions have to be satisfied for it to be detected. First, the event has to scatter at such an angle that it hits a detector surface. Second, after the scatter, the gamma ray has to have an energy within the detection window (i.e., above the lower level energy discriminator (LLD)). In view of these two detection conditions, the majority of the outside-the-FOV events come from the immediately adjacent bed positions because the probability of scatter (i.e., the scatter cross-section) is greater for smaller scatter angles and because scattered events originating in the immediately adjacent bed position can scatter at larger angles and still be detected. Accordingly, it is computationally most efficient to only consider outside-the-FOV activity from immediately adjacent bed positions even though a small amount of outside-the-FOV activity can come from bed positions that are even farther away.

In a full-body PET scan, multiple adjacent bed positions are measured. Thus, when performing scatter correction for the part of the full-body PET scan at a given bed positions, the two scans for the bed positions immediately neighboring (i.e., anterior/above and posterior/below) the bed position can be used generate the outside-the-FOV attenuation maps and activity densities used to perform the outside-the-FOV scatter correction.

In contrast, this information (e.g., the outside-the-FOV attenuation maps and activity densities) is not typically available in single-bed scans (herein the phrase single-bed scan refers to a scan at a single scan position. Accordingly, the methods herein remedy this deficiency by performing short PET scans at the extended position immediately anterior and posterior to the bed position of the single scan. Based on these short extended scans, outside-the-FOV attenuation maps and activity densities can be generated and used to perform outside-the-FOV scatter correction.

For example, scans such as brain or cardiac scans typically involve a limited axial FOV (one or two bed positions). In which case, there is no emission or attenuation map information from outside of the FOV, and outside-the-FOV scatter correction cannot be performed without this information.

One solution to this problem is to perform additional full PET and/or CT scans of the adjacent regions. This solution, however, both increases the total PET scan time and the CT radiation dose (e.g., up to a factor of three when three bed positions are scanned instead of one).

Another possible solution is to determine the activity and attenuation maps outside of the field of view by extrapolating them from the known activity and attenuation maps inside of the field of view. For example, a constant value extrapolation could be used in which the activity and attenuation maps outside of the field of view are set to a constant value equal to the value at the edge slices. This possible solution, however, would result in an inexact approximation to the actual activity and attenuation values outside of the FOV, leading to scatter estimation errors and quantitative biases, especially if activity outside-the-FOV differs significantly from that inside of the FOV.

Accordingly, in a preferred embodiment, the methods described herein provide better estimations of the activity and attenuation values outside of the FOV by using short-extended scans to acquire information regarding the outside-the-FOV regions. Further, the methods described herein acquire this information regarding the outside-the-FOV regions without performing full PET/CT scans of those regions, while still enabling outside-the-FOV scatter correction.

In view of the above, the methods described herein have the advantageous effects of reducing the additional PET scan time as well as reducing the CT radiation dose while simultaneously providing sufficiently accurate outside-the-FOV scatter estimation. The methods described herein achieve these advantageous effects using one or more of the following three approaches. In a first approach, a short-time PET scan is performed in the extended axial FOV (e.g. a short 30 second PET scan) to determine the emission distribution and subsequently the scatter estimation. Further, in the extended axial FOV, the first approach includes a low-dose CT scan to determine the attenuation map in the extended axial FOV.

In a second approach, a short-time PET scan in the extended axial FOV is also performed to determine the emission density, and the attenuation map in the extended axial FOV is then estimated based on an atlas of attenuation maps (e.g., by using an atlas that is selected to best match the patient's size). That is, for the region outside of the imaging FOV (i.e., in the extended FOV) the emission density (also referred to as activity distribution) is obtained from the short extended PET scan, and the attenuation map is obtained from the atlas.

In a third approach, the short-time PET scan is again performed in the extended axial FOV. Then a joint-estimation method is used to estimate both the attenuation map and the emission density from the emission data. That is, the joint-estimation method generates both the emission density and the attenuation map in the extended axial FOV.

The advantage of using the short time PET scan in the extended axial FOV is that so doing minimizes the additional scan time, while the TOF nature of the emission data minimizes attenuation errors from the low-dose CT scan. The duration of the short PET scan is preferably long enough to allow for approximate activity estimates that are sufficient for scatter correction, but that are significantly shorter than that required for an accurate PET image reconstruction.

Figure 3:
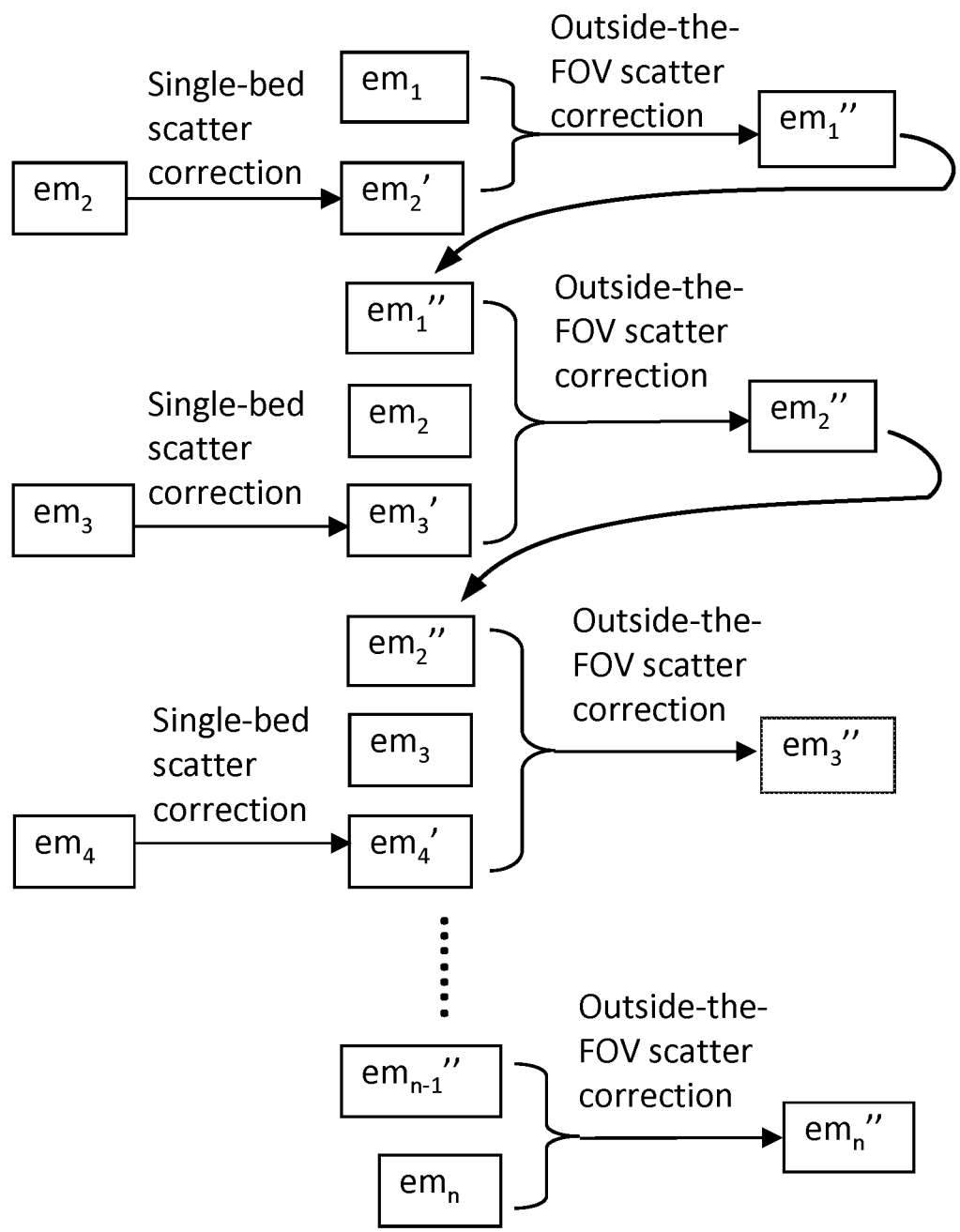
FIG. 3 shows an example of a flow diagram of scatter correction for a multi-bed PET scan, according to one implementation.

FIG. 3 shows an example of a flow diagram for a few-bed scatter correction (for scatter originating from within the FOV and from outside the FOV). In a PET scan with many bed positions, the scatter correction can be performed using the respective PET scans at each bed location. First, activity and attenuation maps are estimated without scatter correction for the FOV in each bed position.

Next, single-bed scatter correction is performed for each bed separately. Single-bed scatter correction refers to the scatter correction performed using the activity and attenuation maps corresponding to only that single bed position. The emission data corrected using only the single-bed scatter correction is referred to as once-corrected data.

Then starting from a bed position at one end of the PET scan (i.e., bed position "1"), an outside-the-FOV scatter correction is calculated at bed position "1" based on the once-corrected emission data at bed position "2," resulting in twice-corrected emission data at bed position "1." Then, the twice-corrected emission data at bed position "1" and the once-corrected emission data at bed position "3" (i.e., the other bed position adjacent to bed position "2") is used to perform outside-the-FOV scatter correction is calculated at bed position "2," resulting in twice-corrected emission data at bed position "2." And the process proceeds at bed position "3" using the twice-corrected emission data at bed position "2" and the once-corrected emission data at bed position "4" to perform outside-the-FOV scatter correction is calculated at bed position "3," and so forth until the emission data at all of the bed positions have been twice corrected (i.e., both single-bed scatter correction and outside-the-FOV scatter correction have been performed).

As shown in the flow diagram for scatter correction in FIG. 3, the few-bed scan includes emission data $em_i$ of n−2 bed positions at which full scans are performed (i.e., the $em_i$ emission data for which i={2, 3, . . . , n−1}) and emission data $em_i$ with i={1,n} corresponding to two short scans in the extended regions. In FIG. 3, $em_i$ represents the uncorrected emission data at the $i^{th}$ position, $em_i'$ represents the once-corrected emission data at the $i^{th}$ position, for which in-the-FOV scatter correction has been performed, and $em_i''$ represents the twice-corrected emission data at the $i^{th}$ position, for which outside-the-FOV scatter correction has been performed. The positions i=1 and i=n are the extended axial FOV bed positions at which short scans are performed, whereas the positions i={2, 3, . . . , n−1} are positions within the few-bed scan at which full scans are performed. Once activity and attenuation maps are estimated for the extended FOV, scatter correction proceeds according to a many-bed protocol. First, emission distributions and attenuation maps are estimated for each bed separately based on the emission data without scatter correction (indicated by $em_i$). Second, single-bed scatter correction is performed for all bed positions such that a series of updated emission distributions are obtained (indicated by $em_i'$). Third, outside-the-FOV scatter estimation is performed using the updated emission distributions and new scatter sinogram estimates are obtained. These are then used to further update emission distributions (indicated by $em_i''$). When a PET/CT scanner is used, the attenuation maps used in the scatter estimation are obtained from the corresponding CT scans of each bed position.

Figure 4A:
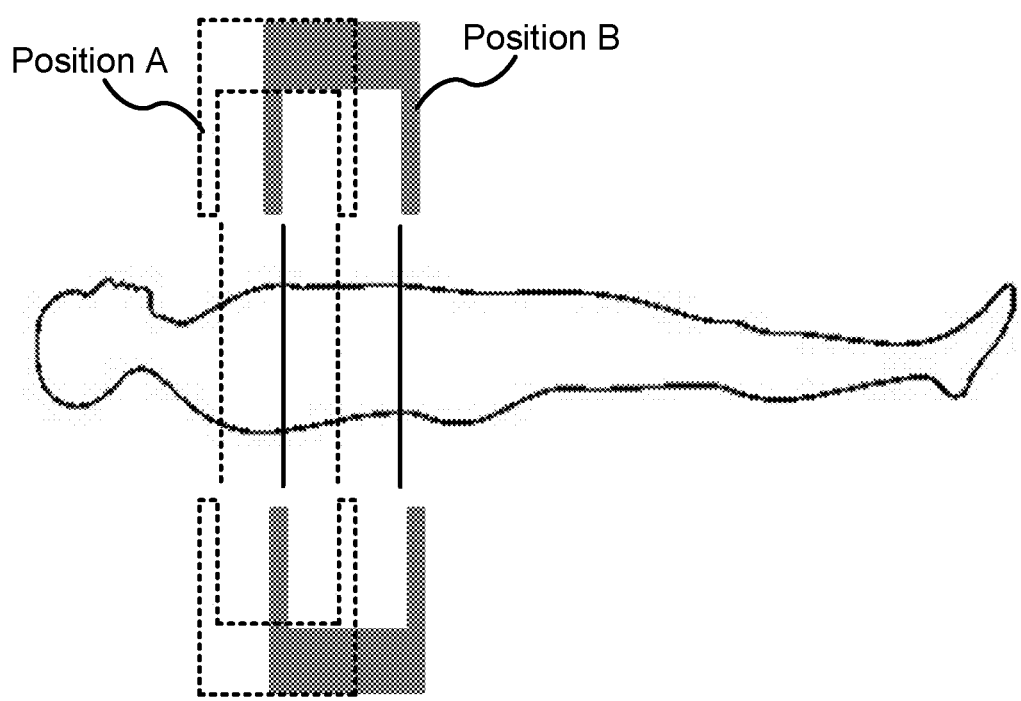
FIG. 4A shows an example of a diagram for a first extended bed position (Position "A") of a PET scanner relative to a bed position for a full PET scan (Position "B"), according to one implementation.
Figure 4B:
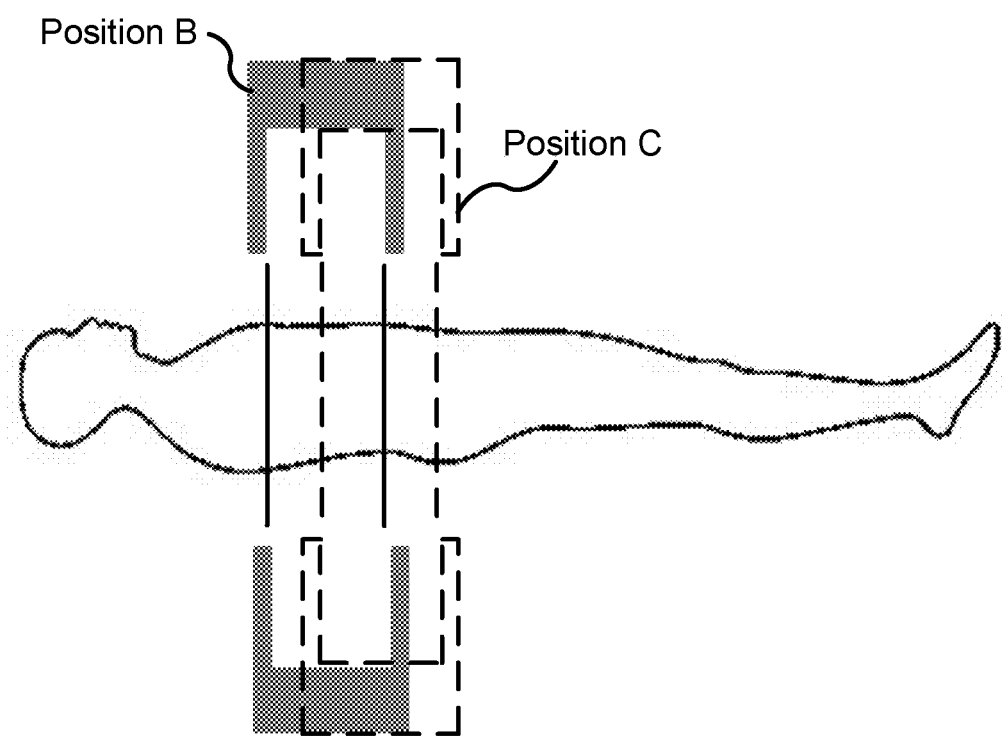
FIG. 4B shows an example of a diagram for a second extended bed position (Position "C") of the PET scanner relative to the bed position for the full PET scan (Position "B"), according to one implementation.

FIGS. 4A and 4B illustrate a non-limiting example of a short-extended scan for PET scan at a single bed position "B." FIG. 4A shows that at position "A" (which is adjacent to and, in certain implementations, overlaps with position "B") a short scan is performed. Similarly, FIG. 4B shows that at position "C" (which also is adjacent to and, in certain implementations, overlaps with position "B") a short scan is performed. In FIGS. 4A and 4B, the regions corresponding to respective bed positions of the PET scanner are labeled using letters, whereas in FIG. 3 the regions are labeled using numbers.

Figure 5:
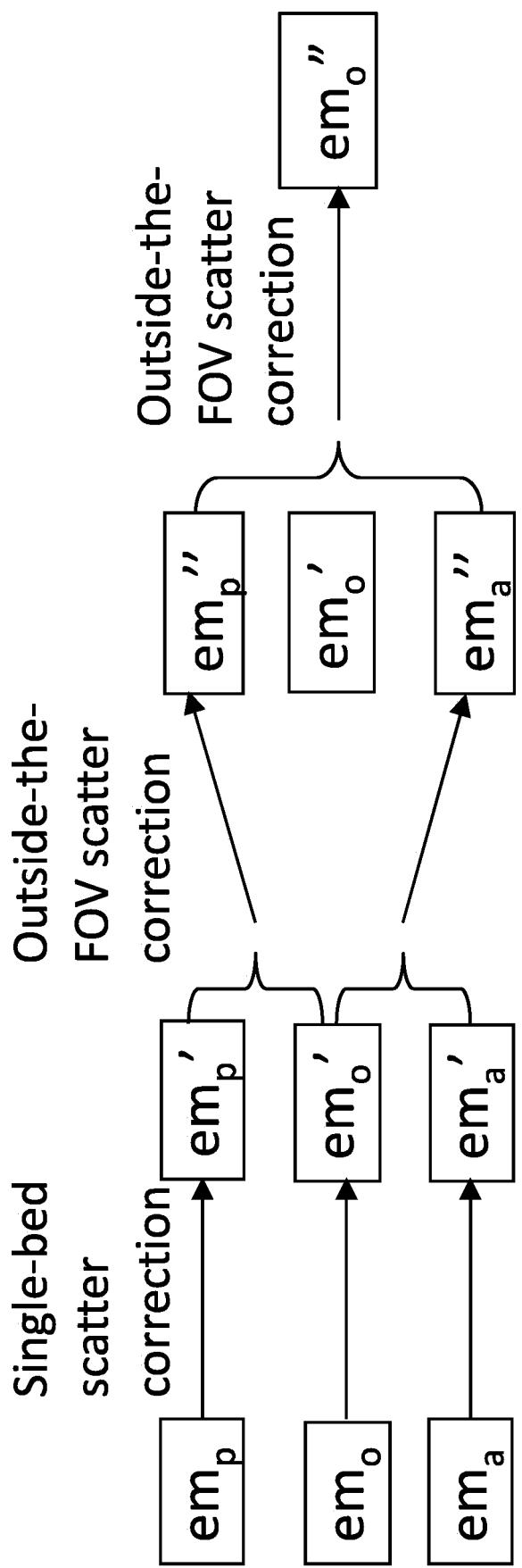
FIG. 5 shows an example of a flow diagram of scatter correction for a single-bed PET scan augmented with short extended scans, according to one implementation.

Further, in FIG. 5, the extended axial FOV regions are denoted by the subscripts "a" and "p," which are short-hand for anterior and posterior. In general, these extended axial FOV regions can also be variously referred to as {proximal, distal}; {anterior, posterior}; and {superior, inferior}. In FIG. 5, the uncorrected emission data at the full-scan FOV is labeled $em_o$, and the uncorrected emission data corresponding to the short-scan regions to either side of the full-scan FOV (e.g., anterior and posterior) are labeled $em_a$ and $em_p$, respectively.

Figure 6:
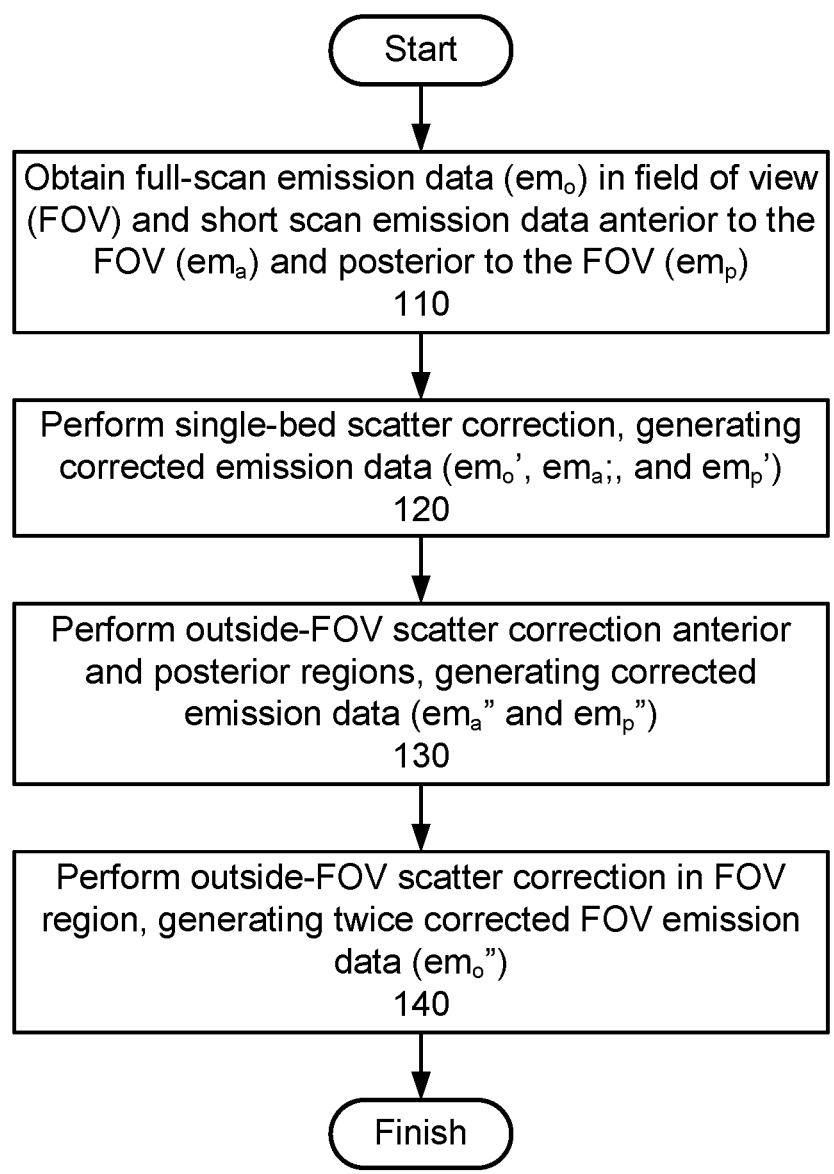
FIG. 6 shows an example of another flow diagram of the scatter correction for the single-bed PET scan augmented with short extended scans, according to one implementation.

FIGS. 5 and 6 show respective flow charts of the process for performing scatter correction when only a full scan is performed at only a single bed position. When the axial FOV of a PET scanner covers the entire of region of interest (ROI), a PET scan of the ROI can be performed with only a single bed position, resulting in no emission data outside of the FOV with which to perform outside-the-FOV scatter correction. Accordingly, to improve the accuracy of outside-the-FOV scatter estimation, a short PET scan can be performed in adjacent regions. In FIG. 5, let the subscripts "p" and "a" denote the two extended short PET scan beds, and let the subscript "o" denote the inside-the-FOV emission data.

The proposed outside-the-FOV scatter correction method for single-bed scan is shown in FIGS. 5 and 6. Starting from the uncorrected emission data $em_o$, $em_a$, and $em_p$, scatter for all beds is estimated using single-bed scatter correction and activity distributions (e.g., the emission data) at all bed positions are updated accordingly, generating the corrected emission data $em_o'$, $em_a'$, and $em_p'$. Next, the attenuation maps and updated activity densities are used to correct the emission data in the extended FOV, generating the twice-corrected emission data $em_a''$ and $em_p''$. Then, the activity densities $em_a''$ and $em_p''$ and the attenuation maps for the outside-the-FOV beds are used to perform outside-the-FOV scatter correction for the bed position of interest, generating the twice-corrected emission data $em_o''$.

FIG. 6 shows that method 100 begins at step 110 with obtaining full-scan emission data ($em_o$) in the FOV and short scan emission data anterior to the FOV ($em_a$) and posterior to the FOV ($em_p$).

At step 120, single-bed scatter correction is performed on all of the emission data, generating corrected emission data $em_o'$, $em_a'$, and $em_p'$.

At step 130, outside-FOV scatter correction is performed on the once-corrected emission data in the anterior and posterior regions, generating twice-corrected emission data $em_a''$ and $em_p''$.

At step 140, outside-FOV scatter correction is performed, using the twice-corrected emission data $em_a''$ and $em_p''$, on the once-corrected emission data $em_o'$, generating twice corrected FOV emission data $em_o''$.

Figure 7B:
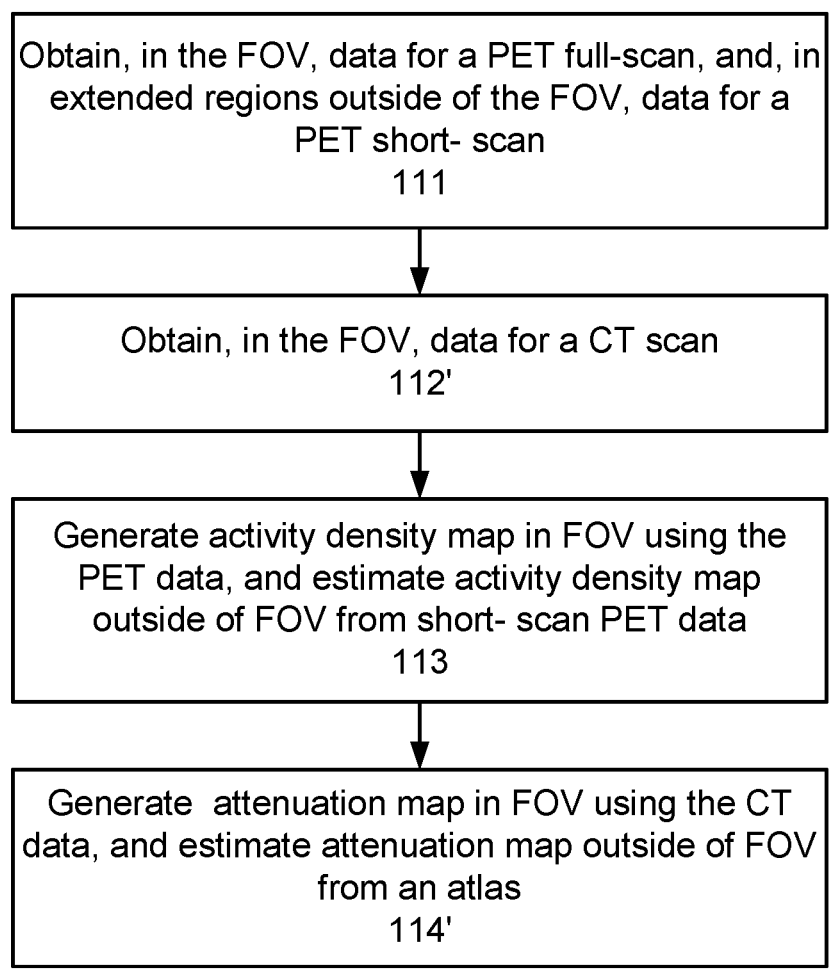
FIG. 7B shows an example of a flow diagram for generating the activity distributions and the attenuation maps using the short PET scans and an atlas of attenuation maps, according to one implementation.

FIGS. 7A, 7B, and 7C show three alternative processes for performing step 110 to determine the initially activity densities and attenuation maps that are subsequently used in method 100 for the scatter correction.

In FIG. 7A, the process of step 110 begins with step 111, in which data from a full PET scan is obtained in the FOV, and data from a short PET scan is obtained in the extended axial region outside of the FOV. In certain implementations, the extended axial region can partially overlap with the FOV, so long as it also extends to the region that is outside of the FOV. For example, the short scans in the extended axial region can each have a 50% overlap with the FOV, according to one non-limiting implementation.

At step 112, data is obtained for a CT scan performed in the FOV. Additionally, data is obtained for a low-dose CT scan performed in the extended axial region outside. When a PET/CT scanner is used the full PET scan and the CT scan in the FOV can be performed simultaneously. Further, the low-dose CT scan and the short PET scan in the extended regions can be performed simultaneously.

At step 113, a map of the activity density (also referred to as the emission distribution) is generated from the obtained PET data. For example, the activity density in the FOV can be reconstructed from the full-scan PET data, and the activity density in the extended regions outside of the FOV can be reconstructed from the short-scan PET data.

At step 114, a map of the attenuation is generated from the obtained CT data. For example, the activity density in the FOV can be reconstructed from the CT data in the FOV, and the attenuation map in the extended regions outside of the FOV can be reconstructed from the low-dose CT data.

In FIG. 7B, the process of step 110 begins with step 111, in which data from a full PET scan is obtained in the FOV, and data from a short PET scan is obtained in the extended axial region outside of the FOV.

At step 112', data is obtained for a CT scan performed in the FOV.

At step 113, a map of the activity density (also referred to as the emission distribution) is generated from the obtained PET data. For example, the activity density in the FOV can be reconstructed from the full-scan PET data, and the activity density in the extended regions outside of the FOV can be reconstructed from the short-scan PET data.

At step 114', a map of the attenuation is generated from the obtained CT data. For example, the activity density in the FOV can be reconstructed from the CT data. There is, however, no CT data for the extended region. Accordingly, an atlas is used to estimate the approximate attenuation profile existing in the extended regions. For example, in certain implementations, the attenuation map determined in the FOV can be used to determine a patient's size and position, which is then used to predict the attenuation profile/map in the extended region, e.g., based on a look-up table (or reference library) of attenuation profiles for patients of varying sizes and body composition. That is, an estimate the attenuation map in the extended axial FOV can be based on which of the attenuation profiles in the atlas most closely matches the patient's size, and the closest attenuation profile from the atlas can then be used to generate the attenuation maps in the extended regions.

In FIG. 7C, the process of step 110 begins with step 111, in which data from a full PET scan is obtained in the FOV, and data from a short PET scan is obtained in the extended axial region outside of the FOV.

At step 115, a joint-estimation method is applied to the PET data to generate both the attenuation maps and the activity distributions for both in and outside of the FOV. That is, the joint-estimation method generates an attenuation map in addition to (e.g., simultaneously with) reconstructing the activity density. That is, applying the joint-estimation method to the data from the full PET scan in the FOV generates the attenuation map and the activity distribution in the FOV. Further, applying the joint-estimation method to the data from the short PET scans generates the attenuation maps and the activity distributions outside of the FOV.

In each of the above implementations of step 110, the shorter scan duration of the short PET scan (and in certain implementations, the lower dosage of the low-dose CT scans) results in the attenuation maps and the activity distributions in the extended regions having lower precision and poorer signal-to-noise ratios (SNRs) than in the FOV, in which a full scan is performed. Nevertheless, these extended-region attenuation maps and activity distributions are sufficient for performing the outside-the-FOV corrections. In certain implementations, the lower signal-to-noise ratios of these maps in the extended regions can be compensated for by using a coarser spatial resolution in the extended regions. Using a low-dose CT scan (or no CT scan, in the case shown in FIG. 7) has the advantage of decreasing the radiation exposure due to additional scans outside of the FOV.

Figure 8A:
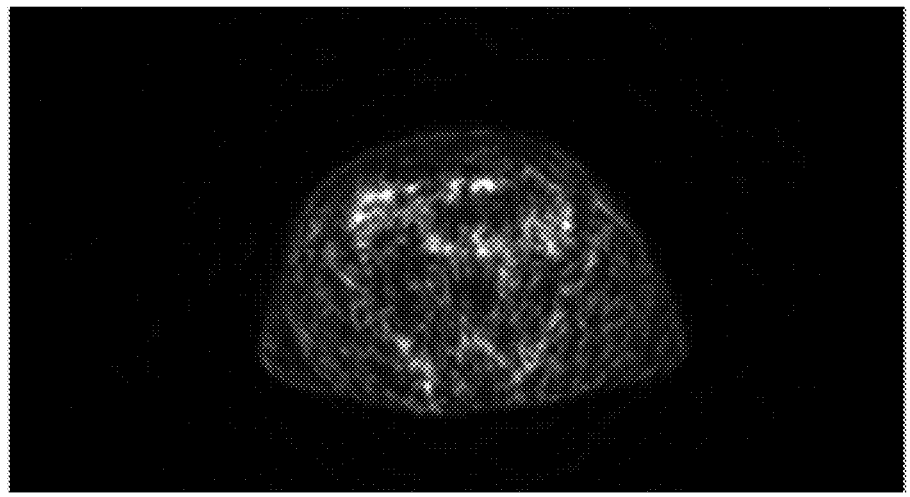
FIG. 8A shows a transverse slice of a reconstructed PET image from a multi-bed scan, according to one implementation.
Figure 8B:
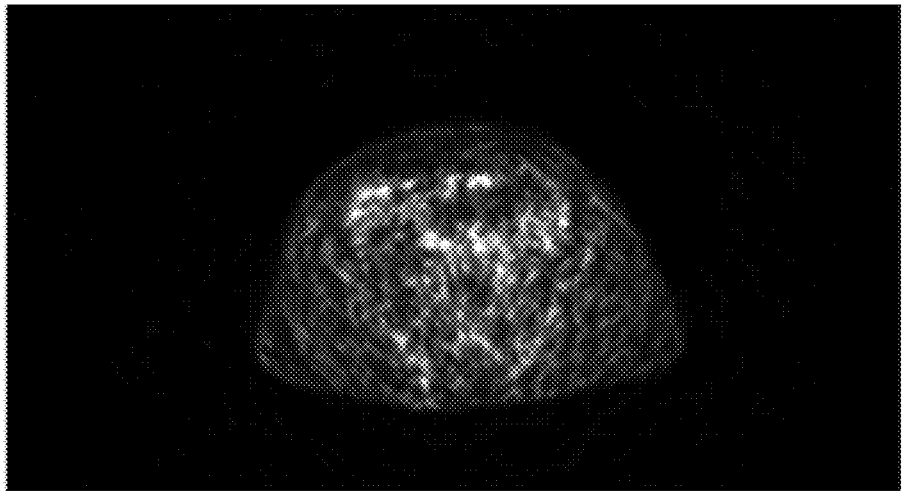
FIG. 8B shows a transverse slice of a reconstructed PET image from a single-bed scan without outside-the-FOV scatter correction, according to one implementation.
Figure 8C:
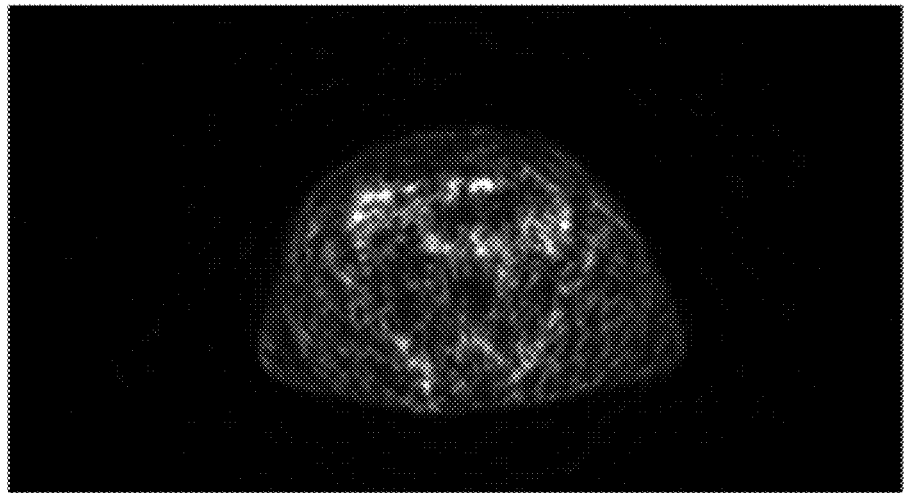
FIG. 8C shows a transverse slice of a reconstructed PET image from a single-bed scan with outside-the-FOV scatter correction based on short PET scans of the extended regions, according to one implementation.

FIGS. 8A, 8B, and 8C show transverse (axial) slices of respective PET images that were reconstructed respectively using (i) a whole-body multi-bed scan including all bed positions, (ii) a single-bed reconstruction without outside-the-FOV scatter corrections, and (iii) a single-bed reconstruction with outside-the-FOV scatter corrections, as described herein with respect to FIGS. 5B and 6. That is, FIG. 8A shows a PET image reconstructed from scanning all of the neighboring bed positions in a whole-body, in which outside-the-FOV scatter was fully corrected for. Accordingly, this can be considered the golden standard for comparison. FIG. 8B shows a PET image reconstructed using a single-bed reconstruction in which no outside-the-FOV scatter correction was performed (e.g., this illustrates the worst case scenario in which outside-the-FOV scatter is neglected). FIG. 8C shows a PET image reconstructed using a reconstruction in which the emission data has been corrected using the activity and attenuation mappings from short PET scans and low-dose CT scans at neighboring/adjacent bed positions. (e.g., the outside-the-FOV scatter is mostly corrected in the reconstructed image, rendering it closer to the fully corrected gold standard).

Figure 9A:
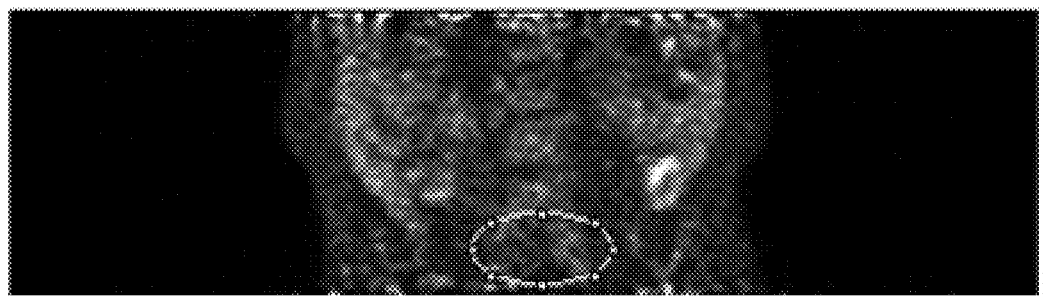
FIG. 9A shows a coronal slice of the reconstructed PET image from the multi-bed scan, according to one implementation.
Figure 9B:
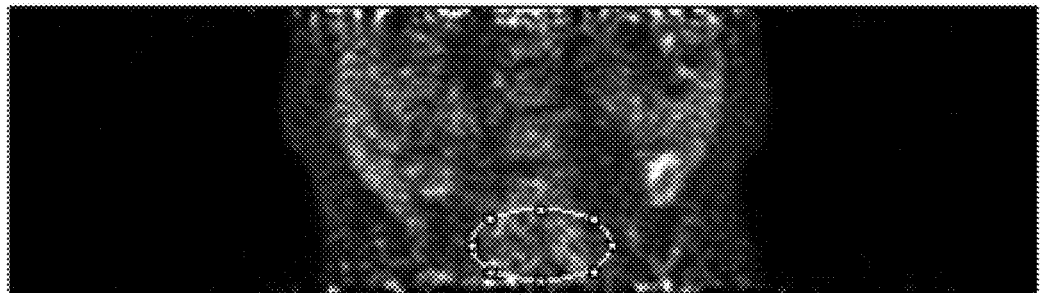
FIG. 9B shows a coronal slice of the reconstructed PET image from the single-bed scan without outside-the-FOV scatter correction, according to one implementation.
Figure 9C:
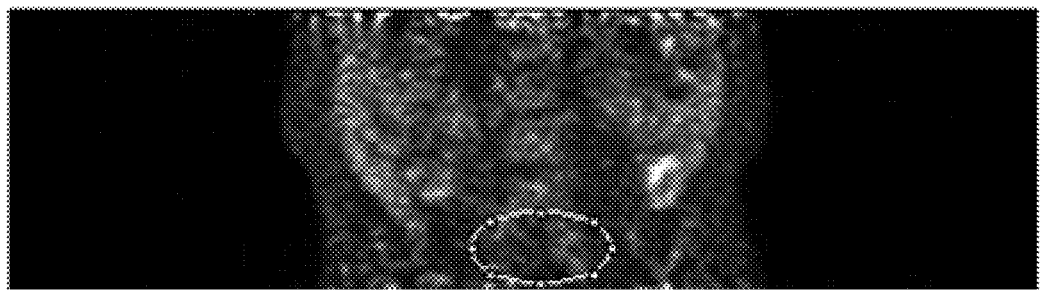
FIG. 9C shows a coronal slice of the reconstructed PET image from the single-bed scan with outside-the-FOV scatter correction based on short PET scans of the extended regions, according to one implementation.

Similarly, FIGS. 9A, 9B, and 9C show frontal (coronal) slices of respective PET images that were reconstructed respectively using (i) a full-body multi-bed scan including all bed positions, (ii) a single-bed reconstruction without outside-the-FOV scatter corrections, and (iii) a single-bed reconstruction with outside-the-FOV scatter correction, as described herein with respect to FIGS. 5 and 6. In each of these figures, a circled region is shown, and in this circled region, (i) the mean activity density is 27.7 for the multi-bed scan result in FIG. 9A, (ii) the mean activity density is 44.1 for the single-bed scan result in FIG. 9B, and (iii) the mean activity density is 26.5 for the extended short scan result in FIG. 9C. Thus, it can be observed that the outside-the-FOV scatter correction generated by the short scan yields good agreement with the gold standard.

As illustrated above, in certain implementations, the methods described herein achieve improved scatter correction in PET imaging by performing outside-the-FOV scatter estimation for regions outside of a full scan volume, but without performing a full scan in the extended regions. That is, rather than performing a full PET scan in these extended volumes, respective short PET scans can be performed instead, and these short extended scans can be used to estimate attenuation maps in the extended volumes/regions. Further, these short extended scans can be used to estimate activity densities in the extended volumes/regions. Both the attenuation maps and the activity densities in the extended regions are used in performing outside-the-FOV scatter correction.

In certain implementations, the PET scanning process includes: (i) determining an axial FOV for a region of interest (ROI), and acquiring a CT scan and a full PET scan of the ROI, and (ii) performing a short PET scan in extended regions adjacent to the ROI. The full PET scan is acquired over a predetermined time duration in order to obtain sufficient count statistics.

In certain implementations, the methods described herein include performing a low-dose CT scan of the extended regions adjacent to the ROI.

In certain other implementations, instead of the low-dose CT scan in the extended regions, the attenuation profile in the extended regions can alternatively be estimated using an atlas or using a joint-attenuation-and-activity-estimation method (also referred to as a joint-estimation method).

In certain implementations, the acquired data in the extended regions is only used to establish estimates of the activity and attenuation maps in regions adjacent to the FOV, and these estimated activity and attenuation maps in the extended regions are only used for the outside-the-FOV scatter corrections—not for PET imaging.

Figure 10:
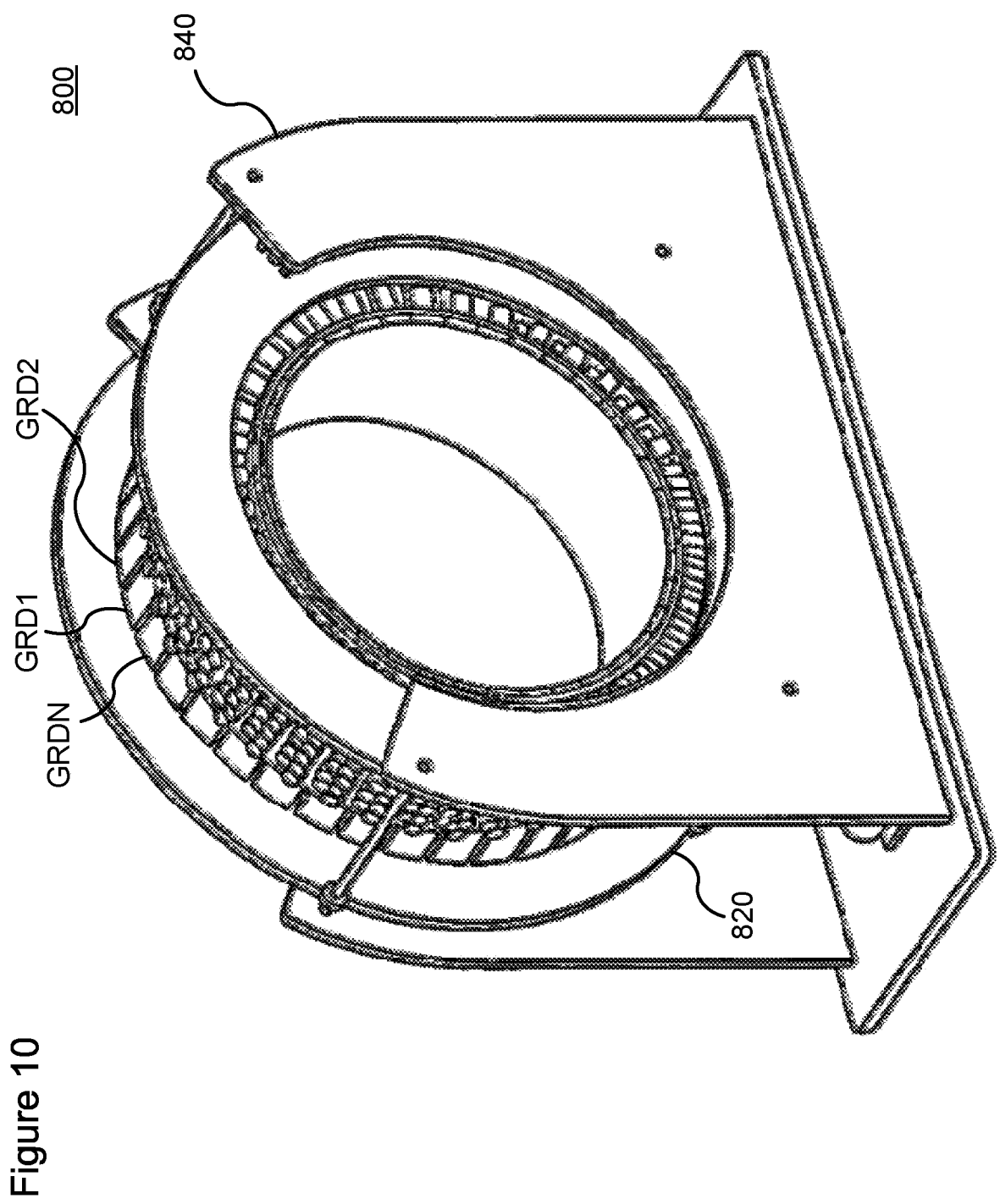
FIG. 10 shows a perspective view of a positron-emission tomography (PET) scanner, according to one implementation.
Figure 11:
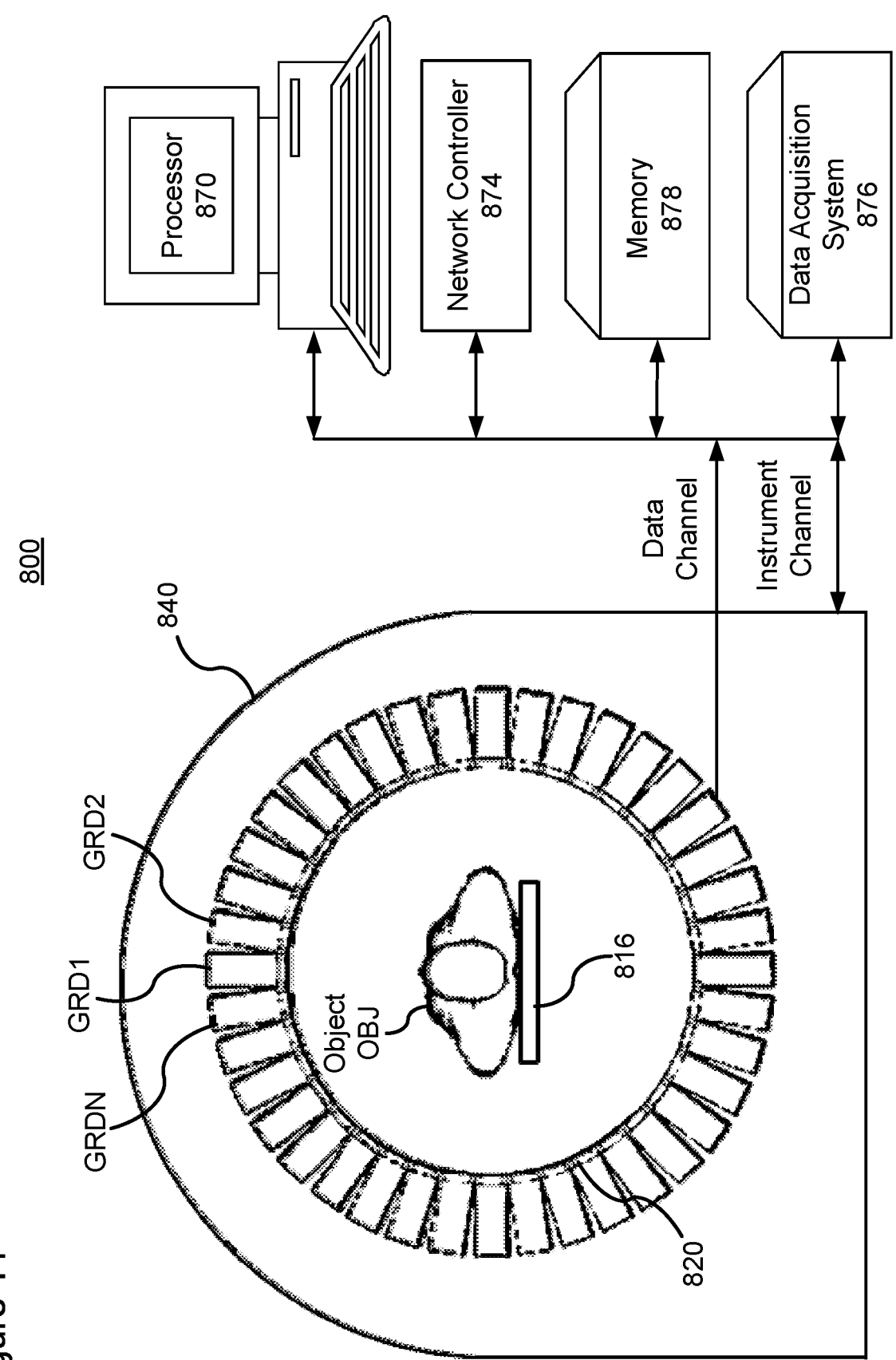
FIG. 11 shows a schematic view of the PET scanner, according to one implementation.

FIGS. 10 and 11 show a PET scanner 800 including a number of GRDs (e.g., GRD1, GRD2, through GRDN) that are each configured as rectangular detector modules. According to one implementation, the detector ring includes 40 GRDs. In another implementation, there are 48 GRDs, and the higher number of GRDs is used to create a larger bore size for the PET scanner 800.

Each GRD can include a two-dimensional array of individual detector crystals, which absorb gamma radiation and emit scintillation photons. The scintillation photons can be detected by a two-dimensional array of photomultiplier tubes (PMTs) that are also arranged in the GRD. A light guide can be disposed between the array of detector crystals and the PMTs. Further, each GRD can include a number of PMTs of various sizes, each of which is arranged to receive scintillation photons from a plurality of detector crystals. Each PMT can produce an analog signal that indicates when scintillation events occur, and an energy of the gamma ray producing the detection event. Moreover, the photons emitted from one detector crystal can be detected by more than one PMT, and, based on the analog signal produced at each PMT, the detector crystal corresponding to the detection event can be determined using Anger logic and crystal decoding, for example.

FIG. 11 shows a schematic view of a PET scanner system having gamma-ray (gamma-ray) photon counting detectors (GRDs) arranged to detect gamma-rays emitted from an object OBJ. The GRDs can measure the timing, position, and energy corresponding to each gamma-ray detection. In one implementation, the gamma-ray detectors are arranged in a ring, as shown in FIGS. 10 and 11. The detector crystals can be scintillator crystals, which have individual scintillator elements arranged in a two-dimensional array and the scintillator elements can be any known scintillating material. The PMTs can be arranged such that light from each scintillator element is detected by multiple PMTs to enable Anger arithmetic and crystal decoding of scintillation event.

FIG. 11 shows an example of the arrangement of the PET scanner 800, in which the object OBJ to be imaged rests on a table 816 and the GRD modules GRD1 through GRDN are arranged circumferentially around the object OBJ and the table 816. The GRDs can be fixedly connected to a circular component 820 that is fixedly connected to the gantry 840. The gantry 840 houses many parts of the PET imager. The gantry 840 of the PET imager also includes an open aperture through which the object OBJ and the table 816 can pass, and gamma-rays emitted in opposite directions from the object OBJ due to an annihilation event can be detected by the GRDs and timing and energy information can be used to determine coincidences for gamma-ray pairs.

In FIG. 11, circuitry and hardware is also shown for acquiring, storing, processing, and distributing gamma-ray detection data. The circuitry and hardware include: a processor 870, a network controller 874, a memory 878, and a data acquisition system (DAS) 876. The PET imager also includes a data channel that routes detection measurement results from the GRDs to the DAS 876, a processor 870, a memory 878, and a network controller 874. The data acquisition system 876 can control the acquisition, digitization, and routing of the detection data from the detectors. In one implementation, the DAS 876 controls the movement of the bed 816. The processor 870 performs functions including reconstructing images from the detection data in accordance with method 100, pre-reconstruction processing of the detection data, and post-reconstruction processing of the image data, as discussed herein.

The processor 870 can be configured to perform method 100 described herein. The processor 870 can include a CPU that can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL, Verilog, or any other hardware description language and the code may be stored in an electronic memory directly within the FPGA or CPLD, or as a separate electronic memory. Further, the memory may be non-volatile, such as ROM, EPROM, EEPROM or FLASH memory. The memory can also be volatile, such as static or dynamic RAM, and a processor, such as a microcontroller or microprocessor, may be provided to manage the electronic memory as well as the interaction between the FPGA or CPLD and the memory.

Alternatively, the CPU in the processor 870 can execute a computer program including a set of computer-readable instructions that perform method 100 described herein, the program being stored in any of the above-described non-transitory electronic memories and/or a hard disk drive, CD, DVD, FLASH drive or any other known storage media. Further, the computer-readable instructions may be provided as a utility application, background daemon, or component of an operating system, or combination thereof, executing in conjunction with a processor, such as a Xenon processor from Intel of America or an Opteron processor from AMD of America and an operating system, such as Microsoft VISTA, UNIX, Solaris, LINUX, Apple, MAC-OS and other operating systems known to those skilled in the art. Further, CPU can be implemented as multiple processors cooperatively working in parallel to perform the instructions.

In one implementation, the reconstructed image can be displayed on a display. The display can be an LCD display, CRT display, plasma display, OLED, LED or any other display known in the art.

The memory 878 can be a hard disk drive, CD-ROM drive, DVD drive, FLASH drive, RAM, ROM or any other electronic storage known in the art.

The network controller 874, such as an Intel Ethernet PRO network interface card from Intel Corporation of America, can interface between the various parts of the PET imager. Additionally, the network controller 874 can also interface with an external network.

As can be appreciated, the external network can be a public network, such as the Internet, or a private network such as an LAN or WAN network, or any combination thereof and can also include PSTN or ISDN sub-networks. The external network can also be wired, such as an Ethernet network, or can be wireless such as a cellular network including EDGE, 3G and 4G wireless cellular systems. The wireless network can also be WiFi, Bluetooth, or any other wireless form of communication that is known.

While certain implementations have been described, these implementations have been presented by way of example only, and are not intended to limit the teachings of this disclosure. Indeed, the novel methods, apparatuses and systems described herein may be embodied in a variety of other forms; furthermore, various omissions, substitutions and changes in the form of the methods, apparatuses and systems described herein may be made without departing from the spirit of this disclosure.

The invention claimed is:

1. An apparatus, comprising:
circuitry configured to
obtain positron emission tomography (PET) data representing gamma rays detected at a plurality of detector elements of a PET scanner, which has field of view (FOV) with respect to coincidence pairs of gamma rays from positron emission, the PET scanner being configured to move a subject with respect the FOV, the PET data including
first emission data of a region of interest (ROI) including one or more full PET scans performed at respective FOVs with respect to the subject, the FOVs spanning the ROI, and each of the one or more full PET scans having a full-scan time duration,
second emission data of a short PET scan performed with the FOV including a first extended region, which is next to the ROI in a first direction, the short PET scan having a short-scan time duration, which is less than the full-scan time duration, and
third emission data of another short PET scan performed with the FOV including a second extended region, which is next to the ROI in an opposite direction to the first direction, the another short PET scan having a duration of the short-scan time duration,
perform single-bed scatter correction on the PET data,
perform, based on the second emission data and the third emission data, outside-the-FOV scatter correction on the first emission data to generate twice-corrected first emission data, and
reconstruct, based on the twice-corrected first emission data, a PET image of the ROI.

2. The apparatus according to claim 1, wherein the circuitry is further configured to
estimate, for each FOV of the PET data, an attenuation map and an activity distribution within the each FOV,
perform, for the each FOV of the PET data, the single-bed scatter correction using the attenuation map and the activity distribution corresponding to the each FOV, and
perform, for each FOV of the first emission data, the outside-the-FOV scatter correction based on the attenuation map and the activity distribution corresponding to adjacent FOVs of the each FOV.

3. The apparatus according to claim 2, wherein the circuitry is further configured to
perform, for an FOV of the second emission data, the outside-the-FOV scatter correction based on the attenuation map and the activity distribution corresponding to an FOV of the first emission data that is adjacent to the FOV of the second emission data, and
perform, for an FOV of the third emission data, the outside-the-FOV scatter correction based on the attenuation map and the activity distribution corresponding to an FOV of the first emission data that is adjacent to the FOV of the third emission data, wherein each of the outside-the-FOV scatter corrections preformed on a respective FOV includes correcting and the activity distribution corresponding to the respective FOV, and the outside-the-FOV scatter correction on the second emission data and on the third emission data are performed prior to the outside-the-FOV scatter correction performed on the first emission data.

4. The apparatus according to claim 2, wherein the circuitry is further configured to perform each of the single-bed scatter corrections to respective FOVs prior to performing any of the outside-the-FOV scatter corrections, and each of the single-bed scatter corrections preformed on a respective FOV includes correcting the activity distribution corresponding to the respective FOV.

5. The apparatus according to claim 2, wherein the circuitry is further configured to perform, for a respective FOV, the outside-the-FOV scatter correction by estimating scatter from outside of the respective FOV based on the activity distribution and the attenuation map within the respective FOV and within adjacent FOVs to the respective FOV.

6. The apparatus according to claim 2, wherein the circuitry is further configured to perform, for a respective FOV, the single-bed scatter correction by estimating scatter from inside of the respective FOV based on the activity distribution and the attenuation map within the respective FOV.

7. The apparatus according to claim 2, wherein the circuitry is further configured to obtain computed tomography (CT) data representing X-rays detected at another plurality of detector elements of a CT scanner, the CT data including first projection data of the ROI, the first projection data being acquired using a first X-ray flux, wherein the attenuation maps corresponding to FOVs of the first emission data are based on CT images that are reconstructed from the first projection data.

8. The apparatus according to claim 7, wherein the circuitry is further configured to obtain the CT data, wherein the CT data includes second projection data of the first extended region, the second projection data being acquired using a low-dose CT scan having a second X-ray flux, which is less than first X-ray flux, and third projection data of the second extended region, the third projection data being that is acquired using a low-dose CT scan having the second X-ray, wherein the attenuation maps corresponding to the FOVs of the second emission data and the third emission data are based on CT images that are reconstructed from the second projection data and third projection data, respectively.

9. The apparatus according to claim 2, wherein the circuitry is further configured to estimate the attenuation map within the each FOV using a joint-estimation method that jointly estimates the attenuation map together with the activity distribution within the each FOV from emission data of the each FOV.

10. The apparatus according to claim 2, wherein the circuitry is further configured to estimate the attenuation map within the each FOV using by selecting from an atlas of attenuation maps an attenuation map that matches a subject of whom the PET data was acquired.

11. The apparatus according to claim 7, wherein the circuitry is further configured to estimate the attenuation map within the each FOV of the second emission data and the third emission data by selecting an attenuation map from an atlas of attenuation maps, the attenuation map being selected to match a subject of whom the PET data was acquired, and the attenuation map being selected based on the attenuation maps corresponding to the FOVs of the first emission data that were reconstructed.

12. An apparatus, comprising:

a display configured to display a reconstructed image;

a bed configured to accommodate a subject that emits gamma rays, the bed being configured to move to respective bed positions;

a plurality of detector elements arranged around the bed and configured to detect, within a field of view, coincident gamma rays from respective positron emissions within the subject, and generate positron emission tomography (PET) data representing coincident gamma-ray detection events at the plurality of detector elements; and circuitry configured to obtain PET data including first emission data of a region of interest (ROI) including one or more full PET scans performed at respective FOVs with respect to the subject, the FOVs spanning the ROI, and each of the one or more full PET scans having a full-scan time duration, second emission data of a short PET scan performed with the FOV including a first extended region, which is next to the ROI in a first direction, the short PET scan having a short-scan time duration, which is less than the full-scan time duration, and third emission data of another short PET scan performed with the FOV including a second extended region, which is next to the ROI in an opposite direction to the first direction, the another short PET scan having a duration of the short-scan time duration, perform single-bed scatter correction on the PET data, perform, based on the second emission data and the third emission data, outside-the-FOV scatter correction on the first emission data to generate twice-corrected first emission data, and reconstruct, based on the twice-corrected first emission data, a PET image of the ROI.

13. A method, comprising:

obtaining positron emission tomography (PET) data representing gamma rays detected at a plurality of detector elements of a PET scanner, which has field of view (FOV) with respect to coincidence pairs of gamma rays from positron emission, the PET scanner being configured to move a subject with respect the FOV, the PET data including first emission data of a region of interest (ROI) including one or more full PET scans performed at respective FOVs with respect to the subject, the FOVs spanning the ROI, and each of the one or more full PET scans having a full-scan time duration, second emission data of a short PET scan performed with the FOV including a first extended region, which is next to the ROI in a first direction, the short PET scan having a short-scan time duration, which is less than the full-scan time duration, and third emission data of another short PET scan performed with the FOV including a second extended region, which is next to the ROI in an opposite direction to the first direction, the another short PET scan having a duration of the short-scan time duration, performing single-bed scatter correction on the PET data;

performing, based on the second emission data and the third emission data, outside-the-FOV scatter correction on the first emission data to generate twice-corrected first emission data; and reconstructing, based on the twice-corrected first emission data, a PET image of the ROI.

14. The method according to claim 13, further comprising:

estimating, for each FOV of the PET data, an attenuation map and an activity distribution within the each FOV, performing, for the each FOV of the PET data, the single-bed scatter correction using the attenuation map and the activity distribution corresponding to the each FOV, and performing, for each FOV of the first emission data, the outside-the-FOV scatter correction based on the attenuation map and the activity distribution corresponding to adjacent FOVs of the each FOV.

15. The method according to claim 14, wherein the performing the outside-the-FOV scatter correction for an FOV of the second emission data is based on the attenuation map and the activity distribution corresponding to an FOV of the first emission data that is adjacent to the FOV of the second emission data, the performing the outside-the-FOV scatter correction for an FOV of the third emission data is based on the attenuation map and the activity distribution corresponding to an FOV of the first emission data that is adjacent to the FOV of the third emission data, each of the outside-the-FOV scatter corrections preformed on a respective FOV includes correcting and the activity distribution corresponding to the respective FOV, and the outside-the-FOV scatter correction on the second emission data and on the third emission data are performed prior to the outside-the-FOV scatter correction performed on the first emission data.

16. The method according to claim 14, wherein each of the single-bed scatter corrections to respective FOVs is performed prior to performing any of the outside-the-FOV scatter corrections, and each of the single-bed scatter corrections preformed on a respective FOV includes correcting the activity distribution corresponding to the respective FOV.

17. The method according to claim 14, further comprising:

obtaining computed tomography (CT) data representing X-rays detected at another plurality of detector elements of a CT scanner, the CT data including first projection data of the ROI, the first projection data being acquired using a first X-ray flux, second projection data of the first extended region, the second projection data being acquired using a low-dose CT scan having a second X-ray flux, which is less than first X-ray flux, and third projection data of the second extended region, the third projection data being that is acquired using a low-dose CT scan having the second X-ray wherein the attenuation maps corresponding to FOVs of the first emission data are based on CT images that are reconstructed from the first projection data, and the attenuation maps corresponding to the FOVs of the second emission data and the third emission data are based on CT images that are reconstructed from the second projection data and third projection data, respectively.

18. The method according to claim 14, wherein the estimating the attenuation map within the each FOV is performed using a joint-estimation method that jointly estimates the attenuation map together with the activity distribution within the each FOV from emission data of the each FOV.

19. The method according to claim 14, wherein the estimating the attenuation map within the each FOV is performed using by selecting from an atlas of attenuation maps an attenuation map that matches a subject of whom the PET data was acquired.

20. A non-transitory computer-readable storage medium including executable instructions, which when executed by circuitry, cause the circuitry to perform the method according to claim 16.

* * * * *